(12) United States Patent
Choi et al.

(10) Patent No.: US 12,318,435 B2
(45) Date of Patent: Jun. 3, 2025

(54) **RECOMBINANT PROTEIN PRODUCED FROM CHOLINESTERASE GENE DERIVED FROM *PSEUDOMONAS AERUGINOSA* AND THE COMPOSITION COMPRISING THE SAME FOR TREATING OR PREVENTING A NEUROLOGICAL DISEASE**

(71) Applicant: SKYPEACH CO., LTD., Seoul (KR)

(72) Inventors: Won Seog Choi, Yongin-si (KR); Moo Hyung Lee, Seoul (KR); Sang-kyun Park, Seoul (KR)

(73) Assignee: SKYPEACH CO., LTD., Seoul (KR)

( * ) Notice: Subject to any disclaimer, the term of this patent is extended or adjusted under 35 U.S.C. 154(b) by 663 days.

(21) Appl. No.: 17/625,727

(22) PCT Filed: Jul. 2, 2020

(86) PCT No.: PCT/KR2020/008646
§ 371 (c)(1),
(2) Date: Jan. 7, 2022

(87) PCT Pub. No.: WO2021/015440
PCT Pub. Date: Jan. 28, 2021

(65) Prior Publication Data
US 2023/0026578 A1    Jan. 26, 2023

(30) Foreign Application Priority Data
Jul. 19, 2019    (KR) ........................ 10-2019-0087620

(51) Int. Cl.
| | |
|---|---|
| *A61K 38/46* | (2006.01) |
| *A61K 45/06* | (2006.01) |
| *A61P 25/00* | (2006.01) |
| *C12N 9/18* | (2006.01) |

(52) U.S. Cl.
CPC ............ *A61K 38/465* (2013.01); *A61K 45/06* (2013.01); *A61P 25/00* (2018.01); *C12N 9/18* (2013.01); *C12Y 301/01007* (2013.01)

(58) Field of Classification Search
CPC ....... A61K 38/465; A61K 45/06; A61P 25/00; C12N 9/18; C12Y 301/01007
See application file for complete search history.

(56) References Cited

PUBLICATIONS

The Quarterly Journal of Defense Policy Studies, 05-01, Jul. 30, 2005.
Lallement G. etc., Effects of soman-induced seizures on different extracellular amino acid levels and on glutamate uptake in rat hippocampus, Brain Res. 563, 234, 1991.
Lallement G. etc., Changes in hippocampal acetylcholine and glutamate extracellular levels during soman-induced seizures: influence of septal cholinoceptive cells, Neurosci. Lett, 139, 104, 1992).
McDonough, J. etc., Atropine and/or Diazepam Therapy Protects against Soman-Induced Neural and Cardiac Pathology, Fund. Appl. Toxicol. 20, 273, 1989.
Shih, T. M. etc., Anticonvulsants for Poisoning by the Organophosphorus Compound Soman:Pharmacological Mechanisms, Neurosci. Biobehav. Rev. 15, 349, 1991.
McDonough, J. etc., Pharmacological Modulation of Soman-Induced Seizures, Neurosci. Biobehav. Rev. 17, 203, 1993.
Garthwaite, G. etc., Neurotoxicity of excitatory amino acid receptor agonists in young rat hippocampal slices, J. Neurosci. Meth. 29, 33, 1989.
Meldrum, B. etc., Exitatory amino acid neurotoxicity and neurodegenerative disease, Tips, 11, 379, 1990.
Upton, N., Mechanisms of action of new antiepileptic drugs: rational design and serendipitous findings, Tips 15, 456, 1994.
Gerlach, M. etc., Neuroprotective Therapeutic Strategies, Biochem. Pharmacol. 50, 1, 1995.
Y. Cho, Pharmacological mechanism and research and development of anti-dote for nerve agent, Journal of the Korea Institute of Military Science and Technology, 14(5), pp. 920-931, Oct. 2011.
Lisa etc., Induction of acid phosphatase and cholinesterase activities in Ps. aeruginosa and their in-vitro control by choline, acetylcholine and betaine, Molecular and Cellular Biochemistry 50, 149-155, 1983.
Lisa A. T., etc., A Glance on Pseudomonas aeruginosa Phosphorylcholine Phosphatase, an Enzyme whose Synthesis Depends on the Presence of Choline in its Environment, Communicating Current Research and Educational Topics and Trends in Applied Microbiology, 255-262, 2007.
Lucchesi G. I. etc., Choline and betaine as inducer agents of Pseudomonas aeruginosa phospholipase C activity in high phosphate medium, FEMS Microbiology Letters 57, 335-338, 1989.
Lucchesi G. I. etc., Carnitine Resembles Choline in the Induction of Cholinesterase, Acid Phosphatase, and Phospholipase C and its Action as an Osmoprotectant in Pseudomonas aeruginosa, Current Microbiology vol. 30, 55-60, 1995.
Domenech C. E., etc., Pseudomonas aeruginosa cholinesterase and phosphorycholine phosphatase: two enzymes contributing to corneal infection, FEMS Microbiology Letter 82, 131-136, 1991.
Kortstee G. J. J., The Aerobic Decomposition of Choline by Microorganisms, Arch. Mikrobiol. 71, 235-244, 1970.
Wargo M. J., etc., Identification of Two Gene Clusters and a Transcriptional Regulator Required for Pseudomonas aeruginosa Glycine Betaine Catabolismournal of Bacteriology, Apr. 2690-2699, 2008.
Sanchez D. G., etc., A Pseudomonas aeruginosa PAO1 acetylcholinesterase is encorded by the PA4921 gene and belongs to the SGNH hydrolase family, Microbiological Research 167, 317-325, 2012.

(Continued)

*Primary Examiner* — Suzanne M Noakes
*Assistant Examiner* — Ciara A McKnight
(74) *Attorney, Agent, or Firm* — NKL Law; Jae Youn Kim

(57) ABSTRACT

The present invention relates to the present invention provides novel recombinant protein produced from cholinesterase gene derived from *Pseudomonas aeruginosa* and the composition comprising the same for treating or preventing a neurological disease.

9 Claims, 1 Drawing Sheet
Specification includes a Sequence Listing.

(56) References Cited

PUBLICATIONS

Ellman G. L, etc., A new and rapid colorimetric determination of acetylcholinesterase activity. Biochem Pharmacology, vol. 7, 88-95, 1961.
Gupta R. C., Carbofuran toxicity, Journal of Toxicology and Environmental Health: Current issue, 43: 4, 383-418, 1994.
International Search Report. PCT/KR2020/008646.

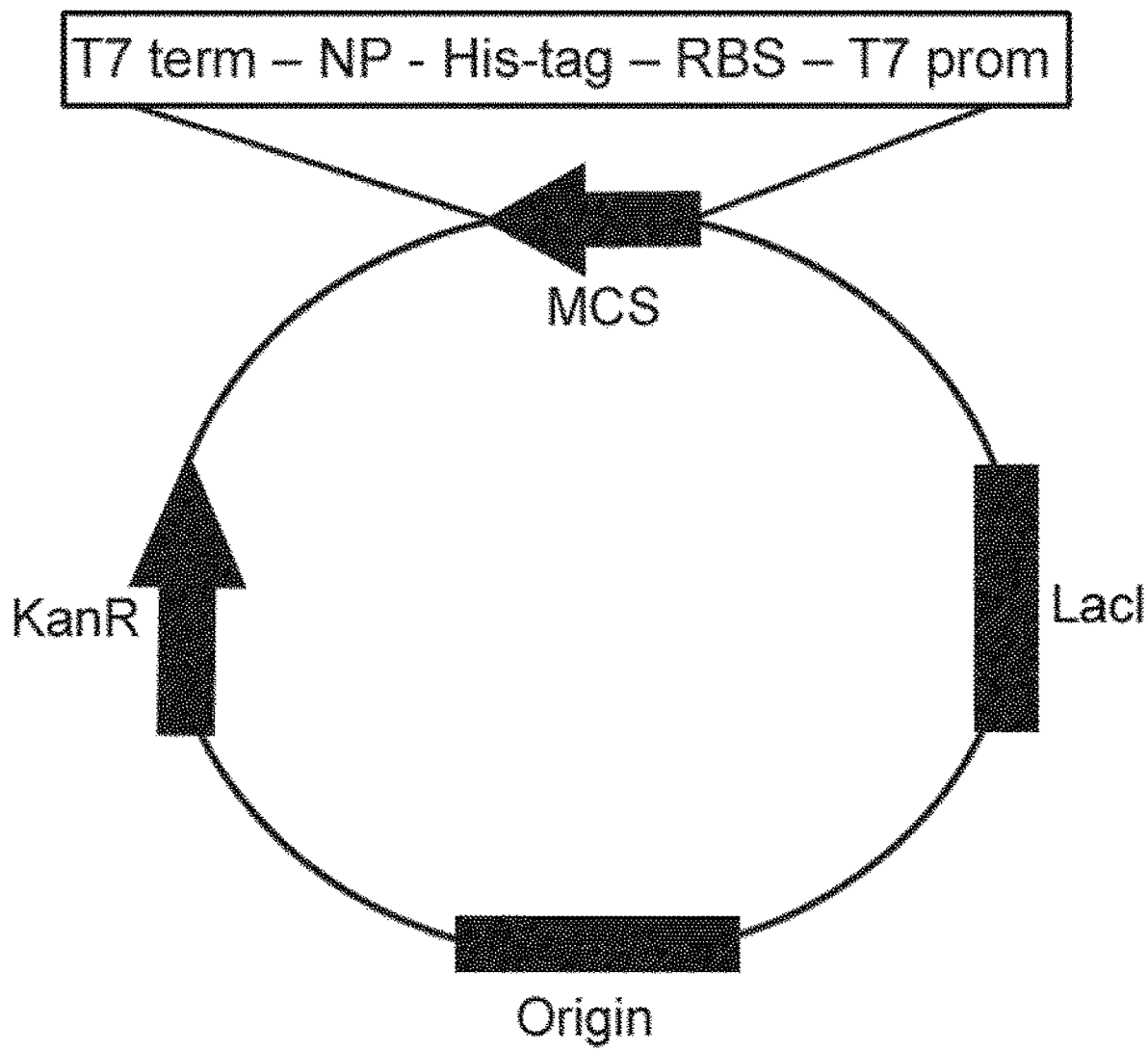

SEQUENCE LISTING

```
<160> NUMBER OF SEQ ID NOS: 4

<210> SEQ ID NO 1
<211> LENGTH: 308
<212> TYPE: PRT
<213> ORGANISM: Pseudomonas aeruginosa

<400> SEQUENCE: 1

Met Gly Ser Ser His His His His His His Ser Ser Gly Leu Val Pro
1               5                   10                  15

Arg Gly Ser His Met His Thr Ser Pro Leu Leu Ala Pro Val Arg Gln
            20                  25                  30

Ile His Ala Phe Gly Asp Ser Tyr Ser Asp Asn Gly Glu Ser Gln Arg
        35                  40                  45

Leu Thr Arg Glu Met Leu Ala Lys Gly Ile Ala Gly Ala Gln Ala Leu
    50                  55                  60

Pro Gly Glu Val Tyr Trp Gln Gly Arg Trp Ser Asn Gly Pro Thr Ala
65                  70                  75                  80

Val Glu Val Leu Ala Arg Gln Leu Gly Ala Gln Leu Ala Asp His Ala
                85                  90                  95

Val Gly Gly Ala Lys Ser Gly Ala Asp Asn Tyr Tyr Ser Trp Met Ser
            100                 105                 110

Ala Tyr Arg His Thr Gly Leu Ala Gly Gln Val Asp Ala Tyr Leu Ala
        115                 120                 125

Thr Leu Asp Gly Lys Pro Val Asp Gly Gln Ala Leu His Phe Ile Phe
    130                 135                 140

Val Ser Ala Asn Asp Phe Phe Glu His Glu Asp Phe Ala Gly Glu Gln
145                 150                 155                 160

Pro Leu Glu Gln Leu Ala Gly Ser Ser Val Ala Asn Ile Arg Ala Ala
```

```
            165                 170                 175
Val Gln Arg Leu Gly Glu Ala Gly Ala Arg Arg Phe Leu Val Val Ser
            180                 185                 190

Ser Thr Asp Leu Ser Val Val Pro Ala Val Val Gly Asn Arg Val
            195                 200                 205

Glu Arg Ala Gln His Tyr Leu Gln Ala Val Asn Ala Ser Leu Pro Ile
            210                 215                 220

Gln Leu Ala Ala Leu Arg Lys Thr Arg Gly Leu Glu Leu Asn Trp Phe
225                 230                 235                 240

Asp His Leu Thr Phe Ser Arg His Leu Arg Arg Asn Pro Ala Arg Tyr
                    245                 250                 255

Gly Leu Val Glu Leu Asp Ala Pro Cys Gln Pro Thr Gln Pro Ser Val
                260                 265                 270

Arg Pro Ala Cys Ala Asn Pro Asp Gln Tyr Tyr Phe Trp Asp Glu Trp
                275                 280                 285

His Pro Thr Arg Arg Val His Gln Leu Ala Gly Glu Ala Met Ala Ala
            290                 295                 300

Arg Tyr Ala Arg
305

<210> SEQ ID NO 2
<211> LENGTH: 927
<212> TYPE: DNA
<213> ORGANISM: Pseudomonas aeruginosa

<400> SEQUENCE: 2
atgggcagca gccatcatca tcatcatcac agcagcggcc tggtgccgcg cggcagccat    60
atgcacacat ccccgctgct cgcgccggta cggcagatcc acgccttcgg cgacagctat   120
tcggacaacg gcgaaagcca gcgactgacc cgcgagatgc tcgccaaggg catcgccggc   180
gcccaggcat tgcccggcga agtctactgg cagggccgct ggagcaacgg cccgaccgcc   240
gtcgaggtgc tcgcccgcca gcttggtgcg caactggccg accatgcggt gggcggcgcc   300
aagagcggag cggacaacta ctacagctgg atgagcgcct accgccatac cggcctcgcc   360
ggccaggtcg acgcctacct cgccacgctg gacggcaagc cggtcgatgg ccaggcgctg   420
cacttcatct tcgtctccgc caacgatttc ttcgagcacg aggatttcgc cggcgagcag   480
cccctggaac aactggccgg cagcagcgtg gcgaacatcc gcgccgcggt gcagcgtctc   540
ggagaggccg cgcacgacg cttcctggtg gtcagttcga ccgacctgag cgtggtcccg   600
gcggtggtcg tcggcaaccg ggtcgagcgt gcgcagcact acctgcaagc ggtcaacgcc   660
agcctgccga tccagctcgc cgccctgcgc aagacccgcg gcctggagct gaactggttc   720
gaccatctca ccttcagccg ccacttgcgg cgcaacccgg cacgctacgg cctggtggag   780
ctggacgcgc cctgccagcc gacccagccc agcgtccgcc cggcctgcgc caacccggac   840
cagtactact ctgggacga gtggcatccg accggcgcg tgcaccaact ggccggcgaa   900
gcgatggcgg cgcgctacgc gcgctga                                       927

<210> SEQ ID NO 3
<211> LENGTH: 21
<212> TYPE: DNA
<213> ORGANISM: Artificial Sequence
<220> FEATURE:
<223> OTHER INFORMATION: synthetic forward primer

<400> SEQUENCE: 3
```

-continued

```
catatgcaca catccccgct g                                                21

<210> SEQ ID NO 4
<211> LENGTH: 21
<212> TYPE: DNA
<213> ORGANISM: Artificial Sequence
<220> FEATURE:
<223> OTHER INFORMATION: synthetic reverse primer

<400> SEQUENCE: 4
ctcgagtcag cgcgcgtagc g                                                21
```

RECOMBINANT PROTEIN PRODUCED FROM CHOLINESTERASE GENE DERIVED FROM *PSEUDOMONAS AERUGINOSA* AND THE COMPOSITION COMPRISING THE SAME FOR TREATING OR PREVENTING A NEUROLOGICAL DISEASE

This application is a U.S. National Phase under 35 U.S.C. § 371 of International Application PCT/KR2020/008646, filed on Jul. 2, 2020, which claims priority to Korean Patent Application No. 10-2019-0087620, filed on Jul. 19, 2019. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention is related to a recombinant protein produced from cholinesterase gene derived from *Pseudomonas aeruginosa* and the composition comprising the same for treating or preventing a neurological disease.

INCORPORATION OF SEQUENCE LISTING

This application contains a sequence listing submitted in Computer Readable Form (CRF). The CRF file contains the sequence listing entitled "Seq.txt", which was created on Jan. 7, 2022 and is 67,735 bytes in size. The information in the sequence listing is incorporated herein by reference in its entirety.

BACKGROUND ART

Nerve agents were first developed for military purposes and were also called neural gases. The mechanism of action occurs by paralyzing the signaling system of the cholinergic mechanism. The irreversible binding paralyzes Acetylcholinesterase (ACHE)'s ability to hydrolyze acetylcholine (ACH).

In the normal case, the ACH that fulfills the mission of signaling must be immediately decomposed by the action of ACHE, but as a result of the irreversible inhibition of ACHE'S function, ACH is accumulated due to excessive accumulation of ACH in the ganglia gap between the central nervous system and peripheral nervous system. The signal is continuously transmitted intensely, showing severe cholinergic toxic effects.

The cholinergic effect stimulates nerve conduction in the early stages, then gradually suppresses nerve transmission, causing paralysis. Difficulty breathing, seizures, cramps, saliva secretion, pupil narrowing, and vomiting can lead to death. These nerve agents can be largely divided into organophosphorus and carbamate, and typical examples include tabun (GA, dimethyl phosphoramidocyanidic acid ethyl ester), sarin (GB, methylphosphonofluoridic acid (1-methylethyl) ester), and soman (GD, methylphosphonofluoridic acid 1,2,2-trimethylpropyl ester), VX (methylphosphonothioic acid S-[2-[bis(1-methylethyl) amino] ethyl]O-ethyl ester), etc. It is used as a main ingredient in agricultural chemicals. (N. T. LEE et al., In vivo toxicity/detoxification mechanism of chemical/detoxifying agents, The Quarterly Journal of Defense Policy Studies, 05-01, Jul. 30, 2005).

To date, as a drug related to a nerve agent, pyridostigmine is used as a treatment agent before poisoning, which irreversibly inhibits about 30% of ACHE resulting in preventing ACHE from being deactivated by a nerve agent. After poisoning, atropine, an anticholinergic drug, competes with ACH competitively with a high affinity for muscarinic receptors. This prevents the choline effect that ACH continuously exerts on the receptor, and 2-PAM (pyridine-2-aldoxime metylchloride) reactivates the inhibited ACHE. However, the most commonly used atropine does not easily overcome the blood-brain barrier, resulting in fatal brain damage even if it survives, and has a limitation that requires a large amount of drugs. In an emergency, intravenous injections should be given, and the first 2 mg dose should be injected intramuscularly and repeated at 10-15 minute intervals. This reduces normal living ability, and asthenia occurs when atropine 6 mg is administered. Excess atropine causes side effects such as hallucinations, ataxia, palpitations, dry mouth, and enlarged pupils. However, there has been no research and development of a therapeutic agent that lowers the level of suddenly increased ACH in the ganglion. Also, to reduce the side effects of atropine, an anticonvulsant diazepam is used, but studies have been published showing that brain protection is insufficient, and there have been reports that the revelation time of the medicinal effect is slow and weak. Since pyridostigmine cannot be absorbed in the brain due to the blood-brain barrier of the central nervous system, it is not possible to expect the effect on the central nervous system, so research on alternative drugs has been continued till now (Y CHO, Pharmacological mechanism and research and development of anti-dote for nerve agent, Journal of the Korea Institute of Military Science and Technology, 14(5), pp 920-931, October, 2011).

Therefore, the therapeutic drug should not be bound to the poisoned nerve agent and should be a substance with the function of ACHE capable of hydrolyzing ACH. Furthermore, it can be used in combination with atropine to reduce overuse and side effects of atropine as well as used as an anticonvulsant. Accordingly, there has been needed for further research and development in that the therapeutic effect can be seen.

On the other hand, acetylcholinesterase (Acetylcholinesterase) is a serine hydrolase to hydrolyze cholinesterase and can be classified according to the sort of each substrate. In humans or animals, cholinesterase decomposes acetylcholine in nerve tissues and muscles. In addition, it is also present in non-cholinergic tissues and body fluids. As a genetic feature, it has Ser/Asp/His catalytic sites and Gly/Asn active sites, thus belonging to the SGNH hydrolase family.

Acetylcholinesterase used in the present invention was found in *Pseudomonas aeruginosa*, and *P. aeruginosa* grows using choline, betaine, and dimethylglycine. For this metabolic process, it produces cholinesterase, acid phosphatase (PchP), and hemolytic phospholipase C (PicH) (Lisa etc., Induction of acid phosphatase and cholinesterase activities in *Ps. aeruginosa* and their in-vitro control by choline, acetylcholine. and betaine, Molecular and Cellular Biochemistry 50, 149-155, 1983; Lisa A T, etc., A Glance on *Pseudomonas aeruginosa* Phosphorylcholine Phosphatase, an Enzyme whose Synthesis Depends on the Presence of Choline in its Environment, Communicating Current Research and Educational Topics and Trends in Applied Microbiology, 255-262, 2007; Lucchesi G I etc., Choline and betaine as inducer agents of *Pseudomonas aeruginosa* phospholipase C activity in high phosphate medium, FEMS Microbiology Letters 57, 335-338, 1989; Lucchesi G I etc., Carnitine Resembles Choline in the Induction of Cholinesterase, Acid Phosphatase, and Phospholipase C and Its Action as an Osmoprotectant in *Pseudomonas aeruginosa*, CURRENT MICROBIOLOGY Vol. 30, 55-60, 1995; Domenech C. E., etc., *Pseudomonas aeruginosa* cholinesterase and phosphorylcholine phosphatase: two enzymes contributing to corneal infection, FEMS Microbiology Letter 82, 131-136, 1991).

The synthesized enzyme catabolizes choline to a nitrogen, carbon and energy source to survive (Kortstee G J J, The Aerobic Decomposition of Choline by Microorganisms, Arch. Mikrobiol. 71, 235-244, 1970; Wargo M J, etc., Identification of Two Gene Clusters and a Transcriptional Regulator Required for *Pseudomonas aeruginosa* Glycine Betaine Catabolism, Journal of BACTERIOLOGY, April, 2690-2699, 2008).

In particular, the similar recombinant protein of *Pseudomonas aeruginosa* PAO1 derived ACHE ac. NP 253608 has been disclosed in the previous literature (Sanchez D G, etc., A *Pseudomonas aeruginosa* PAO1 acetylcholinesterase is encoded by the PA4921 gene and belongs to the SGNH hydrolase family, Microbiological Research 167, 317-325, 2012).

However, the similar recombinant protein has also technical problem to solve, i.e., maintaining activity of ACHE without being inhibited by organophosphorus and carbamate-based nerve agents, differently from the technical effect of the present invention.

However, there has been not reported or disclosed on novel recombinant protein produced from cholinesterase gene derived from *Pseudomonas aeruginosa* that maintains ACHE activity without being inhibited by organophosphorus and carbamate-based nerve agents and the overexpressed protein to enable mass production of ACHE and the therapeutic effect of the protein for treating or preventing a neurological disease in any of above cited literatures, the disclosures of which are incorporated herein by reference.

DISCLOSURE

Technical Problem

Accordingly, the present inventors have studied on the role of ACHE for symptoms or diseases caused by excess and deficiency of choline and ACHE sensitive to organophosphorus and carbamate-based nerve agents, and finally, found novel recombinant protein that maintains ACHE activity without being inhibited by organophosphorus and carbamate-based nerve agents and the overexpressed protein to enable mass production of ACHE and furthermore, confirmed that (1) the produced ACHE was not inhibited by organophosphorous and carbamate compounds, (2) it showed safety through cell experiments and (3) the symptoms of organophosphorus and carbamate-based neurotoxicity-inducing compounds are alleviated and treated through animal experiments, thus, the protein can be used for the treatment of neurological system diseases as well as used as a prophylactic and therapeutic agent, or as a therapeutic agent for organophosphorous and carbamate pesticide poisoning in the present invention.

Technical Solution

The technical solution to solve the problem of the background art is for the development of novel recombinant protein of SEQ ID NO: 1 (designated as NP protein hereinafter) that maintains ACHE activity without being inhibited by organophosphorus and carbamate-based nerve agents, which is produced from cholinesterase gene derived from *Pseudomonas aeruginosa*.

According to one aspect, the present invention provides novel recombinant protein of SEQ ID NO: 1 (designated as NP protein hereinafter) that maintains ACHE activity without being inhibited by organophosphorus and carbamate-based nerve agents, which is produced from cholinesterase gene of SEQ ID NO: 2 (designated as NP gene hereinafter) derived from *Pseudomonas aeruginosa*.

According to the other aspect, the present invention also provides novel cholinesterase gene of SEQ ID NO: 2 (designated as NP gene hereinafter) encoding the recombinant protein of SEQ ID NO: 1 (designated as NP protein hereinafter) that maintains ACHE activity without being inhibited by organophosphorus and carbamate-based nerve agents, which is produced from derived from *Pseudomonas aeruginosa*.

Another object of the present invention provides a production method for producing a large amount of a recombinant protein of cholinesterase, characterized in that the recombinant protein of SEQ ID NO: 1, is excessively induced in *E. coli*.

According to one aspect, the present invention provides a treating agent or a pharmaceutical composition comprising the recombinant protein of SEQ ID NO: 1, as an active ingredient for treating or preventing a poisoning by nerve agents, preferably a poisoning by chemical warfare agent; or a neurological system disorder, preferably, neurological system disorder caused by cholinergic effect, preferably, pesticide poisoning, more preferably, pesticide poisoning caused by organophosphorus and carbamate-based pesticide.

According to one aspect, the present invention provides a therapeutic agent or a treatment aid for treating or preventing a poisoning by nerve agents, preferably a poisoning by chemical warfare agent; or a neurological system disorder, preferably, neurological system disorder caused by cholinergic effect, preferably, pesticide poisoning, more preferably, pesticide poisoning caused by organophosphorus and carbamate-based pesticide using the cholinesterase recombinant protein (SEQ ID NO: 1, NP protein) as an active ingredient.

It is the other object of the present invention to provide a method of treating or preventing a poisoning by nerve agents, preferably a poisoning by chemical warfare agent; or a neurological system disorder, preferably, neurological system disorder caused by cholinergic effect, preferably, pesticide poisoning, more preferably, pesticide poisoning caused by organophosphorus and carbamate-based pesticide in a subject, comprising administering to a subject in need thereof, a treating agent or composition comprising a recombinant protein of SEQ ID NO: 1, as an active ingredient.

It is another object of the present invention to provide a use of a recombinant protein of SEQ ID NO: 1, as an active ingredient for use in the manufacture of medicament employed for treating or preventing a poisoning by nerve agents, preferably a poisoning by chemical warfare agent; or a neurological system disorder, preferably, neurological system disorder caused by cholinergic effect, preferably, pesticide poisoning, more preferably, pesticide poisoning caused by organophosphorus and carbamate-based pesticide in human or mammal.

The present invention also provides a health functional food comprising a recombinant protein of SEQ ID NO: 1, as an active ingredient for the prevention or improvement of a poisoning by nerve agents, preferably a poisoning by chemical warfare agent; or a neurological system disorder, preferably, neurological system disorder caused by cholinergic effect, preferably, pesticide poisoning, more preferably, pesticide poisoning caused by organophosphorus and carbamate-based pesticide.

Specifically, the term "poisoning by nerve agents" disclosed herein comprises all the poisoning by nerve agents, for example, not intended to limit thereto, a poisoning by chemical warfare agent including GA (tabun; dimethylphosphoramidocyanidic acid ethyl ester), GB {sarin, methylphosphonofluoridic acid (1-methylethyl) ester)}, GD (soman, methylphosphonofluoridic acid 1,2,2-trimethylpropyl ester), GE (0-isopropyl-methyl-phosphonofluoridate), GF (cyclohexyl sarin, methylphosphonofluoridic acid cyclohexyl ester), VX {methylphosphonothioic acid S-[2-[bis(1-methylethyl) amino] ethyl] O-ethyl ester)}, VE {S-(Diethylamino) ethyl O-ethyl ethylphosphonothioate}, VG {Tetram; O, O -diethyl S-[2-(diethylamino) ethyl]phosphorothioate}, VM (Edemo; 5-[2-(Diethylamino) ethyl] O-ethyl methylphosphonothioate) and the like.

Specifically, the term "neurological system disorder, preferably, neurological system disorder caused by cholinergic effect" disclosed herein comprises all the a neurological system disorder, for example, not intended to limit thereto, (1) acute cholinergic neurological symptoms, (2) excitatory cranial nerve damage caused by inhibition of y-aminobutyric acid (GABA) receptor, (3) organophosphate-induced delayed polyneuropathy due to neurotoxic esterase inhibition; specifically, respiratory distress due to bronchoconstriction, convulsions, hypersecretion and respiratory muscle paralysis due to suppression of the respiratory center, pesticide poisoning, cramping, headache, hyperhidrosis, incontinence, irritable disease, tic disorder, early dementia symptoms, Parkinson's disease, asthma, cholinergic urticaria disease, and the like.

Specifically, the term "pesticide poisoning caused by organophosphorus and carbamate-based pesticide" disclosed herein comprises all the pesticide poisoning caused by organophosphorus and carbamate-based pesticide, for example, not intended to limit thereto, a pesticide poisoning caused by organophosphorus-based pesticide including parathion, malathion, methyl parathion, chlorpyrifos, diazinon, dichlorvos, phosmet, fenitrothion, tetrachlorvinphos, azamethiphos, azinphos-methyl terbufos etc and carbamate-based pesticide including Propoxur (Baygon®), carbofuran (Furadan®), aldicarb (Temik®), carbaryl (Sevin®), ethienocarb, fenobucarb, oxamyl, methomyl etc.

An inventive recombinant protein may be prepared in accordance with the following preferred embodiment.

For example, the present invention also provides a method for preparing the inventive recombinant protein comprising the steps of, amplifying an NP gene, preferably a cholinesterase NP gene (SEQ ID NO: 2) isolated from genomic DNA of cells selected from the group consisting of *Pseudomonas aeruginosa, Pseudomonas fluorescence, Clostridium botulium, Methylobacterium, Legionella, Nostoc* genus *Burkholderia, Aeromonas, Gossipium, Maize* and *Arabidopsis* by a polymerase chain reaction technique (PCR) to afford PCR product at the first step; after inserting the PCR product obtained in the above step 1 into the TA cloning vector, cloning in host cells selected from the group consisting of Host *E. coli* DH5a, yeast, animal cell line, and identifying their gene sequences at the second step; transferring the gene whose sequence was confirmed in the above step 2, to expression vector such as pET28a using by restriction enzyme such as Ndel (xhol) and then transforming BL21 (DE3) to induce their expression for 10 hours to 36 hours, preferably 14 hours to 20 hours with IPTG (Isopropyl P-D-1-thiogalactopyranoside) at the third step; collecting the expressed cells cultured in step 3 with a centrifuge, lysing them with an ultrasonicator, and purifying them using affinity columns using ions such as HisTrap™ column (GE healthcare), Ni, Co, and Cu at the fourth step; after the purification process of the fourth step, removing salt using a column such as a HiTrap™ Desalting column (GE healthcare), Sephadex gel chromatography column or dialysis column, and performing further purification by replacing the buffer with PBS (phosphate buffered saline at the fifth step; and determining the concentration of purified protein obtained in the fifth step by using the determination method such as Bradford method or Bicinchoninate (BCA) method using bovine serum albumin (BSA) as a standard substance to prepare inventive recombinant protein of the present invention.

It is another object of the present invention to provide a process for preparing the inventive recombinant protein of the present invention as described above for the preparation of composition effective in treating or preventing the purposed diseases.

It is still another object of the present invention to provide a pharmaceutical composition or health functional food comprising the inventive recombinant protein as an active ingredient for preventing and treating purposed disease.

The inventive composition of the present invention shows potent treating effect on a neurological system disorder, preferably, neurological system disorder caused by cholinergic effect or the agrochemical poisoning by nerve agents, preferably, pesticide, more preferably, pesticide poisoning caused by organophosphorus and carbamate-based nerve agents, which is confirmed by various experiments, for example, the present inventors found that novel recombinant protein maintains ACHE activity without being inhibited by organophosphorus and carbamate-based nerve agents and the overexpressed protein to enable mass production of ACHE and furthermore, confirmed that (1) the produced ACHE was not inhibited by organophosphorous and carbamate compounds, (2) it showed safety through cell experiments and (3) the symptoms of organophosphorus and carbamate-based neurotoxicity-inducing compounds are alleviated and treated through various experiments, for example, determination of the inhibitory activity on ACHE activity inhibitor (Experimental Example 1), determination of the survival rate in pesticide-exposed animal model (Experimental Example 2), determination of the blood level of choline in pesticide-exposed animal model (Experimental Example 3), determination of the change in ACHE activity (Experimental Example 4) etc.

Accordingly, it has been confirmed that the inventive recombinant protein can be used for the treatment of neurological system diseases as well as used as a prophylactic and therapeutic agent, or as a therapeutic agent for organophosphorous and carbamate pesticide poisoning in the present invention.

The pharmaceutical composition for treating purposed diseases could contain about 0.01 to 99 w/w % the above protein of the present invention based on the total weight of the composition.

However, the amount and each component of the above-mentioned composition can be varied with the patient's condition, development of patient's disease, the sort of disease etc.

The inventive composition may additionally comprise conventional carrier, adjuvants or diluents in accordance with a using method.

The inventive composition according to the present invention can be formulated in oral dosage form such as powder, granule, tablet, capsule, suspension, emulsion, syrup, aerosol and the like; topical preparation; or injection solution. The inventive composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, magnesium stearate and mineral oil. The formulations may additionally include excipients such as fillers, bulking agents, binders, wetting agents, disintegrating agents, surfactants, diluents and the like. The solid oral dosage form comprises tablet, pill, powder, granule, capsule and the like and the solid oral dosage form is prepared by adding at least one excipient such as starch, calcium carbonate, sucrose, lactose or gelatin and the like to the inventive protein. Lubricant such as magnesium stearate or talc may be used. The aqueous oral dosage form comprises suspension, oral solution, emulsion, syrup and the aqueous oral dosage form may comprise several excipients such as wetting agents, sweetener flavoring agents, preservatives, as well as water, liquid paraffin. The parenteral dosage form comprises sterilized aqueous solution, non-aqueous solvent, suspension, emulsion, lyophilized preparation, suppository, and the like. Suitable examples of the carriers include propylene glycol, polyethylene glycol, vegetable oils such as olive oil, injectable ester such as ethyl oleate. Base for suppository may include witepsol, macrogol, tween 61, cacao butter, laurin, glycerogelatine etc., but are not limited to them.

The desirable dose of the inventive composition varies depending on the condition and the weight of the subject, severity, drug form, route and period of administration, and may be chosen by those skilled in the art. However, in order to obtain desirable effects, it is generally recommended to administer at the amount ranging 0.01 mg/kg to 10 g/kg, preferably, 1 mg/kg to 1 g/kg by weight/day of the inventive composition of the present invention. The dose may be administered in a single or multiple doses per day.

The pharmaceutical composition of present invention can be administered to a subject animal such as mammals (rat, mouse, domestic animals or human) via various routes. All modes of administration are contemplated, for example, administration can be made orally, rectally or by intravenous injection.

The present invention also provides a treating agent, pharmaceutical composition, treatment aid, or health functional food comprising a combination of recombinant protein of SEQ ID NO: 1 and the existing therapeutic agent for nervous system disorder, as an active ingredient for the prevention or improvement of a poisoning by nerve agents, preferably a poisoning by chemical warfare agent; or a neurological system disorder, preferably, neurological system disorder caused by cholinergic effect, preferably, pesticide poisoning, more preferably, pesticide poisoning caused by organophosphorus and carbamate-based pesticide.

Specifically, the term "existing therapeutic agent for nervous system disorder" disclosed herein comprises all the existing therapeutic agent for nervous system disorder, for example, not intended to limit thereto, existing therapeutic agent for nervous system disorder includes pyridostigmine, anticholinergic agents such as benztropine, hyoscine (scopolamine) and atropine, pyridonium oxime such as 2-PAM, sedatives of the central nervous system such as diazepam; enzymes or enzyme inhibitors such as enzyme scavenger, ACHE (acetylcholinesterase), BCHE (butylcholinesterase), CaE (Carboxylesterase), exogenous enzyme, and the like.

In accordance with one aspect of the present invention, there provided a health functional food comprising a recombinant protein of SEQ ID NO: 1 as an active ingredient for the prevention or improvement of a poisoning by nerve agents, preferably a poisoning by chemical warfare agent; or a neurological system disorder, preferably, neurological system disorder caused by cholinergic effect, preferably, pesticide poisoning, more preferably, pesticide poisoning caused by organophosphorus and carbamate-based pesticide.

The term "a health functional food" defined herein comprises the functional food having enhanced functionality such as physical functionality or physiological functionality by adding the inventive protein of the present invention to conventional food to prevent or improve the purposed diseases in human or mammal and stipulated by the Law for Health Functional Foods 6727 in Republic of Korea.

The health functional food composition for preventing and improving purposed diseases could contain about 0.01 to 95 w/w %, preferably 1 to 80 w/w % of the inventive protein composition of present invention based on the total weight of the composition.

Moreover, the inventive protein of the present invention also can be used as a main component or additive and aiding agent in the preparation of various functional health food and health supplement food for the prevention or improvement of a purposed treating disease.

The inventive health functional food may be prepared and processed by the form of pharmaceutically acceptable dosage form such as powder, granule, tablet, capsule, pills, suspension, emulsion, syrup and the like; or the functional health food form such as tea bag, leached tea, health beverage type and the like.

It is the other object of the present invention to provide a health supplement food comprising the recombinant protein of SEQ ID NO: 1, as a main component, for the prevention or improvement of a poisoning by nerve agents, preferably a poisoning by chemical warfare agent; or a neurological system disorder, preferably, neurological system disorder caused by cholinergic effect, preferably, pesticide poisoning, more preferably, pesticide poisoning caused by organophosphorus and carbamate-based pesticide.

The above-mentioned term "as a main component" means that the above health supplement food comprises about 30 to 99 (w/w %), preferably 50 to 99 (w/w %), more preferably 70 to 99 (w/w %) of the inventive protein of present invention based on the total weight of the composition.

When the inventive protein of the present invention is used as a component in the health functional beverage composition, the health functional beverage composition can comprise other component such as flavoring agent or natural carbohydrate without limits like that typical beverage composition. Examples of the natural carbohydrate comprise monosaccharide such as glucose, fructose etc; disaccharide such as maltose, sucrose etc; and polysaccharide, for example, sugar such as dextrin, cyclodextrin, and sugar alcohol such as xylitol, sorbitol, erythritol. Natural flavoring agent (thaumatin, *stevia* extract (rebaudioside A, glycyrrhizin, etc)) and synthetic flavoring agent (saccharin, aspartame, etc) may be added in the health functional beverage composition. The amount of natural carbohydrate generally ranges from about 1 to 20 g, preferably about 5 to 12 g per 100 ml of the present composition.

When the inventive protein of the present invention is used as a food additive of the health food, the combined herb extract may be added intact or used with other food ingredient according to general process. Examples of the food comprises meat products, sausage, bread, chocolate, candy, snack, cracker, biscuit, pizza, ramen, noodle products, chewing gum, dairy products such as ice cream, soup, beverage, tea, drinks, alcohol drink, vitamin complex etc, but not intended herein to limit thereto, for preventing or improving of purposed disease.

The other components than aforementioned composition are various nutrients, a vitamin, a mineral or an electrolyte, synthetic flavoring agent, a coloring agent and improving agent in case of cheese, chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition.

Also, above described protein can be added to food or beverage for prevention and improvement of purposed disorder. The amount of above described protein in food or beverage as a functional health food or health supplement food may generally range from about 0.01 to 15 w/w % of total weight of food for functional health food composition. And the protein of the present invention may be added 0.02 to 5 g, preferably 0.3 to 1 g per 100 ml in health beverage composition.

Advantageous Effects

As described in the present invention, inventive protein composition shows potent treating effect on the poisoning by nerve agents, preferably a poisoning by chemical warfare agent; or a neurological system disorder, preferably, neurological system disorder caused by cholinergic effect, preferably, pesticide poisoning, more preferably, pesticide poisoning caused by organophosphorus and carbamate-based pesticide, which is confirmed by various experiments, for example, the present inventors found that novel recombinant protein maintains ACHE activity without being inhibited by organophosphorus and carbamate-based nerve agents and the overexpressed protein to enable mass production of ACHE and furthermore, confirmed that (1) the produced ACHE was not inhibited by organophosphorous and carbamate compounds, (2) it showed safety through cell experiments and (3) the symptoms of organophosphorus and carbamate-based neurotoxicity-inducing compounds are alleviated and treated through various experiments, for example, determination of the inhibitory activity on ACHE activity inhibitor (Experimental Example 1), determination of the survival rate in pesticide-exposed animal model (Experimental Example 2), determination of the blood level of choline in pesticide-exposed animal model (Experimental Example 3), determination of the change in ACHE activity (Experimental Example 4) etc.

Therefore, the inventive protein of the present invention can be usefully used in a pharmaceutical composition, health functional food, and health supplement food for preventing and treating a poisoning by nerve agents or a neurological system disorder.

BRIEF DESCRIPTION OF DRAWINGS

FIG. 1 depicts the expression procedure of inventive NP protein (cloning diagram).

BEST MODE FOR CARRYING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Examples and Experimental Examples are intended to further illustrate the present invention without limiting its scope.

Example 1. Preparation of Inventive NP Protein (Table 1)

1-1. Expression and Purification of NP Protein

NP gene (SEQ ID NO: 2) from the genomic DNA of *Pseudomonas aeruginosa* (KCCM no. 11328, Korea Microbial Conservation Center) was amplified with PCR amplifier (Thermal cycler, Bioer Technology) using a primer-1 (5'-CAT ATG CAC ACA TCC CCG CTG-3; SEQ ID NO: 3), and primer-2 (5'-CTC GAG TCA GCG CGC GTA GCG-3'; SEQ ID NO: 4). The obtained PCR product was inserted into the TA cloning vector (Cat. No. RC013, RBC), cloned into host *E. coli* DH5a (Cat. No. RH617, RBC) and the NP gene sequence (sequences) was confirmed by analysis.

The NP gene whose sequence was confirmed, was transferred to PET28a (an expression vector, Cat. No. 69864-3CN, novagen) using a restriction enzyme (Nde I, Cat. No. R006, Xho Cat. No. R007, enzynomics) and the gene was recombined into a vector containing six histidines (6 His) in order to facilitate expression. (See FIG. 1)

The recombinant NP plasmid was transformed with BL21 (DE3) (Cat. No. 69450, Novagen) and the gene expression was induced with 0.4 mM IPTG (Isopropyl β-D-1-thiogalactopyranoside, Cat. No.) for 18 hours.

The cultured cells were collected through a centrifuge (1730R, LABOGENE), lysed with an ultrasonic processor (Coprotech Korea) at low temperature, and purified using HisTrap™ column (Cat. No. 29051021, GE healthcare) to determine the solubility of the enzyme.

Purification was performed by removing the salt using a HiTrap™ Desalting column (Cat. No. 29048684, GE healthcare) and replacing the buffer with PBS (phosphate buffered saline).

Protein concentration was measured according to the Bradford method (Cat. No. 5000006, Bio-rad) using bovine serum albumin (BSA; Bo5000 serum albumin, A500023, Biobasic) as a standard.

Through the above purification process, purified cholinesterase recombinant protein (SEQ ID NO: 1) was obtained (95% or more purity, designated as "NP protein" hereinafter), which are used as a test samples in following experiment.

TABLE 1

Sequence List

| SEQ ID NO | Sequence |
|---|---|
| 1 | Met Gly Ser Ser His His His His His His Ser Ser Gly Leu Val Pro Arg Gly Ser His Met His Thr Ser Pro Leu Leu Ala Pro Val Arg Gln Ile His Ala Phe Gly Asp Ser Tyr Ser Asp Asn Gly Glu Ser Gln Arg Leu Thr Arg Glu Met Leu Ala Lys Gly Ile Ala Gly Ala Gln Ala Leu Pro Gly Glu Val Tyr Trp Gln Gly Arg Trp Ser Asn Gly Pro Thr Ala Val Glu Val Leu Ala Arg Gln Leu Gly Ala Gln Leu Ala Asp His Ala Val Gly Gly Ala Lys Ser Gly Ala Asp Asn Tyr Tyr Ser Trp Met Ser Ala Tyr Arg His Thr Gly Leu Ala Gly Gln Val Asp Ala Tyr Leu Ala Thr Leu Asp Gly Lys Pro Val Asp Gly Gln Ala Leu His Phe Ile Phe Val Ser Ala Asn Asp Phe Phe Glu His Glu Asp Phe Ala Gly Glu Gln Pro Leu Glu Gln Leu Ala Gly Ser Ser Ala Asn Ile Arg Ala Ala Val Gln Arg Leu Gly Glu Ala Gly Ala Arg Arg Phe Leu Val Val Ser Ser Thr Asp Leu Ser Val Val Pro Ala Val Val Val Gly Asn Arg Val Glu Arg Ala Gln His Tyr Leu Gln Ala Val Asn Ala Ser Leu Pro Ile Gln Leu Ala Ala Leu Arg Lys Thr Arg Gly Leu Glu Leu Asn Trp Phe Asp His Leu Thr Phe Ser Arg His Leu Arg Arg Asn Pro Ala Arg Tyr Gly Leu Val Glu Leu Asp Ala Pro Cys Gln Pro Thr Gln Pro Ser Val Arg Pro Ala Cys Ala Asn Pro Asp Gln Tyr Tyr Phe Trp Asp Glu Trp His Pro Thr Arg Arg Val His Gln Leu Ala Gly Glu Ala Met Ala Ala Arg Tyr Ala Arg |
| 2 | ATGGGCAGCA GCCATCATCA TCATCATCAC AGCAGCGGCC TGGTGCCGCG CGGCAGCCAT ATGCACACAT CCCCGCTGCT CGCGCCGGTA CGGCAGATCC ACGCCTTCGG CGACAGCTAT TCGGACAACG GCGAAAGCCA GCGACTGACC CGCGAGATGC TCGCCAAGGG CATCGCCGGC GCCCAGGCAT TGCCCGGCGA AGTCTACTGG CAGGGCCGCT GGAGCAACGG CCCGACCGCC GTCGAGGTGC TCGCCCGCCA GCTTGGTGCG CAACTGGCCG ACCATGCGGT GGGCGGCGCC AAGAGCGGAG CGGACAACTA CTACAGCTGG ATGAGCGCCT ACCGCCATAC CGGCCTCGCC GGCCAGGTCG ACGCCTACCT CGCCACGCTG GACGGCAAGC CGGTCGATGG CCAGGCGCTG CACTTCATCT TCGTCTCCGC CAACGATTTC TTCGAGCACG AGGATTTCGC CGGCGAGCAG CCCCTGGAAC AACTGGCCGG CAGCAGCGTG GCGAACATCC GCGCCGCGGT GCAGCGTCTC GGAGAGGCCG GCGCACGACG CTTCCTGGTG GTCAGTTCGA CCGACCTGAG CGTGGTCCCG GCGGTGGTCG TCGGCAACCG GGTCGAGCGT GCGCAGCACT ACCTGCAAGC GGTCAACGCC AGCCTGCCGA TCCAGCTCGC CGCCCTGCGC AAGACCCGCG GCCTGGAGCT GAACTGGTTC GACCATCTCA CCTTCAGCCG CCACTTGCGG CGCAACCCGG CACGCTACGG CCTGGTGGAG CTGGACGCGC CCTGCCAGCC GACCCAGCCC AGCGTCCGCC CGGCCTGCGC CAACCCGGAC CAGTACTACT TCTGGGACGA GTGGCATCCG ACCCGGCGCG TGCACCAACT GGCCGGCGAA GCGATGGCGG CGCGCTACGC GCGCTGA |
| 3 | primer-1: 5'-CAT ATG CAC ACA TCC CCG CTG-3' |
| 4 | primer-2: 5'-CTC GAG TCA GCG CGC GTA GCG-3' |

Experimental Example 1. Determination of the Inhibitory Activity on ACHE Activity Inhibitor In order to determine the inhibitory activity of the inventive NP protein on ACHE activity inhibitor, following test was performed by the Ellman esterase assay disclosed in the literature (Ellman G L, Courtney K D, Andres V, Feather-Stone RM. A new and rapid colorimetric determination of acetylcholinesterase activity. Biochem Pharmacol. 1961 July; 7:88-95).

1-1. Test Procedure

PBS (LB004-01, Welgene) was used as a negative control group and ACHE extracted from eel (Cat. No., C3389, Sigma) was used as positive control group.

100 mM NaHPO4 (pH 8.6, SP1010, Geogiachem.) was used as a buffer solution and 75 mM acetylthiocholine (Cat. No., A5626, Sigma) was used as a substrate.

10 mM DTNB {5,5'-Dithiobis (2-nitrobenzoic acid), Cat. No., D8130, Sigma} was used for developing agent. trichlorfon (Cat. No., 45698, Sigma) was used as an organophosphorus-based pesticide and both of Carbofuran (Cat. No.,
32056, Sigma) and propoxur (Cat. No., 45644, Sigma) were used as carbamate-based pesticide.

225 μL of buffer solution, 3 μL of acetylthiocholine, 7.5 μL of DTNB and 14.5 μL of sterilized distilled water were mixed together. 50 μL of ACHE (NP or ACHE from eel) was added to the solution to the extent that total volume of the reaction solution reached to 300 μL and reacted together for 5 mins at 25° C. to determine the absorbance of the solution at 412 nm using by spectrometer (Multiskan Go., Thermo Scientific).

The inhibitory activity of the inventive NP protein as well as the positive control group containing Trichlrofon or Carbofuran on ACHE activity inhibitor was determined by comparing with the absorbance of negative control group.

1-2. Test Result

As can be seen Table 2, it has been confirmed that the ACHE activity in the test group treated with NP protein was not inhibited by organophosphorous and carbamate compounds, while the ACHE activity in the control group treated with ACHE extracted with eel together with various pesticides (Trichlorfon, Carbofuran, Propoxur) was reduced by about 85-96%.

TABLE 2

Inhibition Activity Of ACHE Activity

| Sample* | Activity rate (%) |
|---|---|
| ACHE (EE) | 100 |
| ACHE (EE) + Carbofuran | 3.4 |
| ACHE (EE) + Propoxur | 25.6 |
| ACHE (EE) + Trichlorfon | 8.7 |
| NP | 100 |
| NP + Carbofuran | 99.3 |
| NP + Propoxur | 99.1 |
| NP + Trichlorfon | 93.8 |

*ACHE (EE): ACHE extracted from eel

Experimental Example 2. Determination of the Survival Rate

In order to determine the survival rate of the inventive NP protein on pesticide-exposed animal model, following test was performed by the procedure disclosed in the literature (Gupta, Ramesh C., 'Carbofuran toxicity', Journal of Toxicology and Environmental Health, Part A, 43:4, pp 383-418, 1994).

2-1. Test Procedure

Specific pathogen-free female ICR mice (about 20 g, aged 6 weeks) were purchased from ORIENT Co. (Seoul, Korea) and acclimated with the experimental environment for 1 week.

250 µg of NP protein was intraperitoneally injected to the mice as a test sample group to observe the behavior of the mice for 40 mins and 30 µg of carbofuran and 9 mg of trichlorfon were intraperitoneally injected to the mice to observe the survival rate of the mice for 30 mins.

The group intraperitoneally injected with only 30 µg of carbofuran or 9 mg of trichlorfon were used as positive control groups to observe the survival rate of the mice and the group intraperitoneally injected with only distilled water containing 250 µg of NP protein was used as a negative control group to observe the survival rate of the mice.

2-2. Test Result

As shown in Table 3, the group pretreated with NP protein showed 100% survival rate whereas the positive control group treated with only carbofuran or trichlorfon showed 0% and 60% survival rate.

TABLE 3

Effect On Survival Rate

| Sample* | Survival rate (%) |
|---|---|
| PBS | 100 |
| NP | 100 |
| Carbofuran | 0 |
| NP + Carbofuran | 100 |
| Trichlorfon | 60 |
| NP + Trichlorfon | 100 |

*PBS: phosphate buffer saline

It has been confirmed that the NP protein showed potent treating or preventing activity from the poisoning by nerve agents or a neurological system disorder respectively.

Experimental Example 3. Determination of the Blood Level of Choline

In order to determine the effect on the blood level of choline of the inventive NP protein in pesticide-exposed animal model, following test was performed by the procedure disclosed in the literature (Choline/Acetylcholine Quantification Colorimetric/Fluorometric Kit, Biovision incorporated 155 S Milpitas Boulevard, Milpitas, Calif. 95035 USA).

3-1. Test Procedure

Specific pathogen-free female ICR mice (about 20 g, aged 6 weeks) were purchased from ORIENT Co. (Seoul, Korea) and acclimated with the experimental environment for 1 week.

The mice used in Experimental Example 2 intraperitoneally injected with 250 g of NP protein as a test sample group, were killed with carbon dioxide gas (Shinyang Oxygen Industry, Korea) and the blood was collected from the heart to isolate the serum.

The choline level of blood serum was determined Choline/Acetylcholine Quantification Colorimetric/Fluorometric Kit (Cat. No. K615-100, Biovision).

1 µL of serum was added to 49 µL of buffer solution in the kit and the reaction mixture containing 444 of buffer solution, 2 µL of choline probe, 2 µL of ACHE and 2 µL of enzyme mixture solution was added thereto to react together in the shadow at 25° C. for 30 mins.

30 mins after the reaction, the absorbance of the reaction solution was determined at 570 nm using by spectrometer (Multiskan Go., Thermo Scientific) and the determined level was transformed into absolute value by comparing with the level of standard curve.

The level of choline was calculated according to following Math. 1

$$\text{Blood Level of choline(nmole/mL or micromole)} = \text{(calculated level of choline through standard curve)/(the amount of samples in each well; mL).} \quad [\text{Math. 1}]$$

3-2. Test Result

As shown in Table 4, the group pretreated with NP protein showed reduced amount of acetylcholine whereas the positive control group treated with only carbofuran or trichlorfon showed sharply increased amount of acetylcholine.

It has been confirmed that the NP protein showed potent treating or preventing activity from the poisoning by nerve agents or a neurological system disorder respectively.

TABLE 4

Change In The Level Of Blood Acetylcholine

| Sample* | Concentration (nmol/mL) |
|---|---|
| PBS | 1.0 |
| NP | 1.5 |
| Carbofuran | 1.8 |
| NP + Carbofuran | 0.5 |
| Trichlorfon | 1.4 |
| NP + Trichlorfon | 0.7 |

*PBS: phosphate buffer saline

Experimental Example 4 Determination of the Change in ACHE Activity

In order to determine the change of ACHE activity of test sample, following test was performed by the Ellman esterase assay disclosed in the literature (Ellman G L, Courtney K D, Andres V, Feather-Stone RM. Anew and rapid colorimetric determination of acetylcholinesterase activity. Biochem Pharmacol. 1961 July; 7:88-95).

4-1. Test Procedure

Specific pathogen-free female ICR mice (about 20 g, aged 6 weeks) were purchased from ORIENT Co. (Seoul, Korea) and acclimated with the experimental environment for 1 week.

The mice used in Experimental Example 2 intraperitoneally injected with 250 g of NP protein as a test sample group, were killed with carbon dioxide gas (Shinyang Oxygen Industry, Korea) and the blood was collected from the heart to isolate the serum.

The choline level of blood serum was determined Choline/Acetylcholine Quantification Colorimetric/Fluorometric Kit (Cat. No. K764-100, Biovision) and ACHE (EE) (Catalog No., C3389, Sigma) extracted from eel was used as a positive control group.

30 μL of serum was added to 20 μL of buffer solution in the kit and the reaction mixture containing 45 μL of buffer solution, 2 μL of choline oxidase enzyme mix solution, 2 μL of ACHE probe and 1 μL of ACHE substrate was added thereto to react with the serum together at 25° C. for 30 mins.

30 mins after the reaction, the absorbance of the reaction solution was determined at every 1 min at 570 nm using by spectrometer (Multiskan Go., Thermo Scientific) and the determined level was calculated according to following Math. 2

$$\text{ACHE activity} = \text{(the definition of 100mU: the amount of enzyme to generate 1.0 nmol choline per 1 min at pH 7.4).} \quad [\text{Math. 2}]$$

4-2. Test Result

As shown in Table 5, the group treated with NP protein showed potently increased sensitivity of ACHE activity by about 100 fold than that of positive control group treated with the identical concentration of ACHE (EE).

It has been confirmed that the NP protein showed potent treating or preventing activity from the poisoning by nerve agents or a neurological system disorder respectively.

TABLE 5

CHANGE IN THE ACHE ACTIVITY

| Sample | Activity ($OD_{412}$) |
| --- | --- |
| PBS | 0 |
| ACHE (EE) (3 μg) | 1.042 |
| NP (0.03 μg) | 1.480 |

* PBS: phosphate buffer saline

As shown in Table 6, the group pretreated with NP protein showed increased ACHE activity comparing with negative control group whereas the positive control group treated with only carbofuran or trichlorfon showed decreased ACHE activity.

It has been confirmed that the NP protein showed potent treating or preventing activity from the poisoning by nerve agents or a neurological system disorder respectively and particularly, the neurological disorder caused by the uncontrolled mechanism of acetylcholine.

TABLE 6

Change In ACHE Activity

| Sample* | Concentration (mU/mL) |
| --- | --- |
| PBS | 591.8 |
| NP | 1,410 |
| Carbofuran | 463.8 |
| NP + Carbofuran | 1,266 |
| Trichlorfon | 117.7 |
| NP + Trichlorfon | 1,051 |

*PBS: phosphate buffer saline

MODE FOR THE INVENTION

Hereinafter, the formulating methods and kinds of excipients will be described, but the present invention is not limited to them. The representative preparation examples were described as follows.

Preparation of Injection
  NP protein: 100 mg
  Sodium metabisulfite: 3.0 mg
  Methyl paraben: 0.8 mg
  Propyl paraben: 0.1 mg
  Distilled water for injection: optimum amount
  Injection preparation was prepared by dissolving active component, controlling pH to about 7.5 and then filling all the components in 2 ml ample and sterilizing by conventional injection preparation method.

Preparation of Powder
  NP protein: 500 mg
  Corn Starch: 100 mg
  Lactose: 100 mg
  Talc: 10 mg
  Powder preparation was prepared by mixing above components and filling sealed package.

Preparation of Tablet
  NP protein 200 mg
  Corn Starch 100 mg
  Lactose 100 mg
  Magnesium stearate optimum amount
  Tablet preparation was prepared by mixing above components and entabletting.

Preparation of Capsule
  NP protein: 100 mg
  Lactose: 50 mg
  Corn starch: 50 mg
  Talc: 2 mg
  Magnesium stearate optimum amount
  Tablet preparation was prepared by mixing above components and filling gelatin capsule by conventional gelatin preparation method.

Preparation of Liquid
  NP protein: 1000 mg
  Sugar: 20 g
  Polysaccharide: 20 g
  Lemon flavor: 20 g
  Liquid preparation was prepared by dissolving active component, and then filling all the components in 1000 ml ample and sterilizing by conventional liquid preparation method.

Preparation of Health Food
  NP protein: 1000 mg
  Vitamin mixture: optimum amount
  Vitamin A acetate: 70 g
  Vitamin E: 1.0 mg
  Vitamin $B_{10}$: 13 mg
  Vitamin $B_2$: 0.15 mg Vitamin B6: 0.5 mg
Vitamin B1: 20.2 g
Vitamin C: 10 mg
Biotin: 10 g
Amide nicotinic acid: 1.7 mg
Folic acid: 50 g
Calcium pantothenic acid: 0.5 mg
Mineral mixture: optimum amount
Ferrous sulfate: 1.75 mg
Zinc oxide: 0.82 mg
Magnesium carbonate: 25.3 mg
Monopotassium phosphate: 15 mg
Dicalcium phosphate: 55 mg
Potassium citrate: 90 mg
Calcium carbonate: 100 mg
Magnesium chloride: 24.8 mg The above mentioned vitamin and mineral mixture may be varied in many ways. Such variations are not to be regarded as a departure from the spirit and scope of the present invention.

Preparation of Health Beverage
NP protein: 1000 mg
Citric acid: 1000 mg
Oligosaccharide: 100 g
Apricot concentration: 2 g
Taurine: 1 g
Distilled water: 900 Mq Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the present invention provides a recombinant protein produced from cholinesterase gene derived from *Pseudomonas aeruginosa* and the composition comprising the same for treating or preventing a neurological disease and the inventive protein showed potent treating effect on the poisoning by nerve agents or a neurological system disorder, which is confirmed by various experiments, for example, determination of the inhibitory activity on ACHE activity inhibitor (Experimental Example 1), determination of the survival rate in pesticide-exposed animal model (Experimental Example 2), determination of the blood level of choline in pesticide-exposed animal model (Experimental Example 3), determination of the change in ACHE activity (Experimental Example 4) etc. Therefore, the inventive protein of the present invention can be usefully used in a pharmaceutical composition, health functional food, and health supplement food for preventing and treating a neurological disease.

The invention claimed is:

1. A recombinant protein of SEQ ID NO: 1 (NP protein) that maintains ACHE activity without being inhibited by organophosphorus and carbamate-based nerve agents, which is produced from cholinesterase gene of SEQ ID NO: 2 (designated as NP gene hereinafter) derived from *Pseudomonas aeruginosa.*

2. A cholinesterase gene of SEQ ID NO: 2 (NP gene) encoding the recombinant protein of SEQ ID NO: 1 (designated as NP protein hereinafter) that maintains ACHE activity without being inhibited by organophosphorus and carbamate-based nerve agents, which is derived from *Pseudomonas aeruginosa.*

3. A pharmaceutical composition comprising the recombinant protein of SEQ ID NO: 1, as an active ingredient for treating or preventing a poisoning by nerve agents or a neurological system disorder.

4. The pharmaceutical composition according to claim 3, wherein said poisoning by nerve agents is a poisoning by chemical warfare agent selected from the group consisting of GA (tabun; dimethylphosphoramidocyanidic acid ethyl ester), GB {sarin, methylphosphonofluoridic acid (1-methylethyl) ester)}, GD (soman, methylphosphonofluoridic acid 1,2,2-trimethylpropyl ester), GE (O-isopropyl-methylphosphonofluoridate), GF (cyclohexyl sarin, methylphosphonofluoridic acid cyclohexyl ester), VX {methylphosphonothioic acid S-[2-[bis (1-methylethyl) amino] ethyl]O-ethyl ester)}, VE {S-(Diethylamino) ethyl O-ethyl ethylphosphonothioate}, VG {Tetram; O, O-diethyl S-[2-(diethylamino) ethyl] phosphorothioate} and VM (Edemo; S-[2-(Diethylamino) ethyl] O-ethyl methylphosphonothioate).

5. The pharmaceutical composition according to claim 3, wherein said neurological system disorder is acute cholinergic neurological symptoms, excitatory cranial nerve damage caused by inhibition of γ-aminobutyric acid (GABA) receptor, or organophosphate-induced delayed polyneuropathy due to neurotoxic esterase inhibition.

6. The pharmaceutical composition according to claim 5, wherein said neurological system disorder is selected from the group consisting of respiratory distress due to bronchoconstriction, convulsions, hypersecretion and respiratory muscle paralysis due to suppression of the respiratory center, pesticide poisoning, cramping, headache, hyperhidrosis, incontinence, irritable disease, tic disorder, early dementia symptoms, Parkinson's disease, asthma, and cholinergic urticaria disease.

7. The pharmaceutical composition according to claim 6, wherein said pesticide is a pesticide poisoning caused by organophosphorus-based pesticide selected from the group consisting of parathion, malathion, methyl parathion, chlorpyrifos, diazinon, dichlorvos, phosmet, fenitrothion, tetrachlorvinphos, azamethiphos, and azinphos-methyl terbufos; or a carbamate-based pesticide selected from the group consisting of Propoxur, carbofuran, aldicarb, carbaryl, ethienocarb, fenobucarb, oxamyl and methomyl.

8. A pharmaceutical composition comprising the recombinant protein of claim 1 and an existing therapeutic agent for nervous system disorder, as an active ingredient for the prevention or improvement of a poisoning by nerve agents or a neurological system disorder.

9. The pharmaceutical composition according to claim 8, wherein said existing therapeutic agent for nervous system disorder is selected from the group consisting of pyridostigmine, benztropine, hyoscine (scopolamine), pyridonium oxime, diazepam, enzyme scavenger, ACHE (acetylcholinesterase), BCHE (butylcholinesterase), CaE (Carboxylesterase) and exogenous enzyme.

* * * * *